United States Patent
Shimamura et al.

(10) Patent No.: US 12,215,109 B2
(45) Date of Patent: Feb. 4, 2025

(54) CRYSTAL OF PYRAZOLO[3,4-D]PYRIMIDINE

(71) Applicant: TAIHO PHARMACEUTICAL CO., LTD., Chiyoda-ku (JP)

(72) Inventors: Tadashi Shimamura, Tsukuba (JP); Hiromi Oshiumi, Tokushima (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 824 days.

(21) Appl. No.: 17/271,424

(22) PCT Filed: Aug. 28, 2019

(86) PCT No.: PCT/JP2019/033647
§ 371 (c)(1),
(2) Date: Feb. 25, 2021

(87) PCT Pub. No.: WO2020/045475
PCT Pub. Date: Mar. 5, 2020

(65) Prior Publication Data
US 2021/0332056 A1    Oct. 28, 2021

(30) Foreign Application Priority Data

Aug. 29, 2018 (JP) .................. 2018-159840

(51) Int. Cl.
*C07D 487/04*    (2006.01)

(52) U.S. Cl.
CPC ........ *C07D 487/04* (2013.01); *C07B 2200/13* (2013.01)

(58) Field of Classification Search
CPC .... C07D 487/04; C07B 2200/13; A61P 35/00
See application file for complete search history.

(56) References Cited

U.S. PATENT DOCUMENTS 9,920,060 B2 *   3/2018   Kawai .................. C07D 487/04
2017/0217970 A1   8/2017   Kawai et al.

FOREIGN PATENT DOCUMENTS

WO    WO 2017/038838 A1    3/2017

OTHER PUBLICATIONS

English et al. HER2 Expression Beyond Breast Cancer: Therapeutic Implications for Gynecologic Malignancies, Mol Diagn Ther. 17:85-99. (Year: 2013).*
Oh et al. HER2-targeted therapies—a role beyond breast cancer. Clinical Oncology, 17, 33-48. (Year: 2020).*
Luo et al. Principles of Cancer Therapy: Oncogene and Non-oncogene Addiction, 136, 823-837. (Year: 2009).*
Extended European Search Report issued Apr. 8, 2022 in European Patent Application No. 19855702.7, 8 pages.
Mino R. Caira, "Crystalline Polymorphism of Organic Compounds" Topics in Current Chemistry, vol. 198, XP008166276, Jan. 1, 1998, pp. 163-208.
G. Patrick Stahly, "Diversity in Single- and Multiple-Component Crystals. The Search for and Prevalence of Polymorphs and Cocrystals" Crystal Growth & Design, vol. 7, No. 6, XP002483372, May 18, 2007, pp. 1007-1026.
Combined Chinese Office Action and Search Report issued Jan. 19, 2023, in corresponding Chinese Patent Application No. 201980056990.1 (with English Translation), 17 pages.
Fang Liang, "Pharmaceutical Science and Technology 3rd Edition", China Medical Science Press, Mar. 2016, pp. 46-60 (with a machine-generated English abstract).
Ashizawa, K. et al., "Polymorphism and crystallization of the pharmaceutical drugs," with partial English translation, Maruzen Planet Co., Ltd. Sep. 20, 2002, pp. 305-317 (20 total pages).
Matsuoka, M. et a., "Base & Application of Polymorphic Crystals," with partial English translation, Popular Edition, First Edition CMC Publishing Co., Ltd., Oct. 22, 2010, pp. 105-117, 181-191 (26 total pages).
International Search Report issued on Nov. 5, 2019 in PCT/JP2019/033647 filed on Aug. 28, 2019, 2 pages.

* cited by examiner

*Primary Examiner* — Matthew P Coughlin
*Assistant Examiner* — Meghan C Heasley
(74) *Attorney, Agent, or Firm* — Oblon, McClelland, Maier & Neustadt, L.L.P.

(57) ABSTRACT

An object of the invention is to provide a crystal of (R)-1-(1-acryloylpiperidin-3-yl)-4-amino-N-(4-(2-(dimethylamino)-2-oxoethyl)-2,3-dimethylphenyl)-1H-pyrazolo[3,4-d]pyrimidine-3-carboxamide which is excellent in stability and preferable from the viewpoint of manufacturing and formulation. The present invention provides a crystal having an X-ray powder diffraction spectrum having characteristic peaks at diffraction angles (2θ±0.2°) of 6.0°, 7.7°, 8.9°, 10.6°, 12.1°, 13.1°, 14.0°, 14.7°, 15.5°, 15.8°, 16.8°, 17.7°, 18.1°, 18.4°, 19.4°, 23.4°, 24.1°, 24.7°, 25.1° and 25.7°.

8 Claims, 9 Drawing Sheets

CRYSTAL OF PYRAZOLO[3,4-D]PYRIMIDINE

This application is a national stage application of PCT/JP2019/033647, filed Aug. 28, 2019, the entire contents of which is incorporated by reference herein. This application claims benefit of Japanese application 2018-159840, filed Aug. 29, 2018, the entire contents of which is incorporated herein by reference.

FIELD OF THE INVENTION

The present invention relates to a crystal of a pyrazolo [3,4-d]pyrimidine compound excellent in storage stability and useful as an antitumor agent, and a pharmaceutical composition comprising the crystal.

BACKGROUND OF THE INVENTION

In general, when a compound is used as an effective active ingredient of a pharmaceutical, the chemical and physical stability of the compound is required in order to keep the quality stable and/or facilitate the storage management. Therefore, the obtained compound is preferably in a stable crystal form and in general the most stable crystal form is often selected as a drug substance for a pharmaceutical.

So far, a plurality of Her2 inhibitors have been reported as an antitumor agent, and Patent Literature 1 describes a pyrazolo[3,4-d]pyrimidine compound (chemical name: (R)-1-(1-acryloylpiperidin-3-yl)-4-amino-N-(4-(2-(dimethylamino)-2-oxoethyl)-2,3-dimethylphenyl)-1H-pyrazolo[3,4-d]pyrimidine-3-carboxamide (hereinafter, also referred to as "Compound (I)") of formula (I):

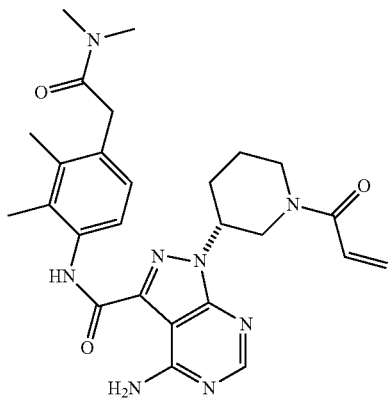

as a compound which has an excellent Her2 inhibitory activity and exhibits antitumor activity.

However, Patent Literature 1 does not describe the crystal form of the compound, and so far, the stable crystal form of compound (I) and the method for manufacturing the crystal form have not been known.

CITATION LIST

Patent Literature

[Patent Literature 1] International Publication No. WO2017/038838

SUMMARY OF THE INVENTION

Problem to be Solved by the Invention

An object of the present invention is to provide a stable crystal form of Compound (I) useful as an antitumor agent.

Means for Solving the Problem

For achieving the object, the present inventors have extensively conducted studies, and resultantly found that Compound (I) has three crystal forms (Crystal I, Crystal II and Crystal III), and of these crystal forms, Crystal I is non-hygroscopic and has excellent solid stability, thereby completing the present invention.

That is, the present invention provides the following [1] to [13].

[1] A crystal of (R)-1-(1-acryloylpiperidin-3-yl)-4-amino-N-(4-(2-(dimethylamino)-2-oxoethyl)-2,3-dimethylphenyl)-1H-pyrazolo[3,4-d]pyrimidine-3-carboxamide having an X-ray powder diffraction spectrum having at least six peaks at diffraction angles (2θ±0.2°) selected from the group consisting of 6.0°, 7.7°, 8.9°, 10.6°, 12.1°, 13.1°, 14.0°, 14.7°, 15.5°, 15.8°, 16.8°, 17.7°, 18.1°, 18.4°, 19.4°, 23.4°, 24.1°, 24.7°, 25.1° and 25.7°.

[2] The crystal according to [1], wherein the crystal has an X-ray powder diffraction spectrum having peaks at diffraction angles (2θ±0.2°) of 6.0°, 7.7°, 8.9°, 10.6°, 12.1°, 13.1°, 14.0°, 14.7°, 15.5°, 15.8°, 16.8°, 17.7°, 18.1°, 18.4°, 19.4°, 23.4°, 24.1°, 24.7°, 25.1° and 25.7°.

[3] The crystal according to [1] or [2], wherein an endothermic peak is present at a peak temperature of around 200° C. in thermogravimetric-differential thermal simultaneous measurement (TG-DTA measurement).

[4] The crystal according to any one of [1] to [3], wherein the crystal has the following crystal data in single-crystal analysis: crystal system: single-crystal system space group: P2₁
lattice constant:
a=11.5696(2) Å
b=7.47792(14) Å
c=14.6722 (3) Å
p=100.674(7°)
Volume of unit lattice: V=1247.43(5) Å³.

[5] A pharmaceutical composition comprising the crystal according to any one of [1] to [4].

[6] The pharmaceutical composition for oral administration, comprising the crystal according to any one of [1] to [4].

[7] An antitumor agent comprising the crystal according to any one of [1] to [4].

[8] Use of the crystal according to any one of [1] to [4], for manufacturing a pharmaceutical composition.

[9] Use of the crystal according to any one of [1] to [4], for manufacturing a pharmaceutical composition for oral administration.

[10] Use of the crystal according to any one of [1] to [4], for manufacturing an antitumor agent.

[11] The crystal according to any one of [1] to [4], for use as a medicament.

[12] The crystal according to any one of [1] to [4], for use in treating a tumor.

[13] A method for treating a tumor, comprising administering an effective amount of the crystal according to any one of [1] to [4] to a patient in need thereof.

Effect of the Invention

The crystal (Crystal I) of (R)-1-(1-acryloylpiperidin-3-yl)-4-amino-N-(4-(2-(dimethylamino)-2-oxoethyl)-2,3-dimethylphenyl)-1H-pyrazolo[3,4-d]pyrimidine-3-carboxamide according to the present invention is superior to other crystal forms in, for example, handling properties (lower in moisture absorption) and/or quality controllability, and is therefore useful when the compound is used as a drug substance for a pharmaceutical.

Crystal I of the present invention is safe as a pharmaceutical because the amount of residual solvents is equal to or lower than the criterion value specified in Guideline for Residual Solvents in Pharmaceuticals in ICH Guideline.

DETAILED DESCRIPTION OF THE INVENTION

The term described merely as "Compound (I)" herein means (R)-1-(1-acryloylpiperidin-3-yl)-4-amino-N-(4-(2-(dimethylamino)-2-oxoethyl)-2,3-dimethylphenyl)-1H-pyrazolo[3,4-d]pyrimidine-3-carboxamide, and is used to in a sense include both an "amorphous material" and a "crystal".

The Compound (I) can be synthesized in accordance with the method described in International Publication No. WO2017/038838, among others.

In the present description, the terms "crystal" and "amorphous material" are used in the usual sense.

For the X-ray powder diffraction pattern, the diffraction angle and the general pattern are important in confirmation of identity of crystals, due to the nature of the data. The relative intensity of the X-ray powder diffraction pattern can slightly vary depending on the crystal growth direction, the particle size and measurement conditions, and therefore should not be taken strictly.

In the values obtained from a variety of patterns, there may be some margins of error depending on the direction of crystal growth, the size of particles, measurement conditions etc. Therefore, in the present description, the value of the diffraction angle (2θ) in the X-ray powder diffraction pattern can have a measurement error within the range of about ±0.2°.

The endothermic peak in a thermogravimetric-differential thermal simultaneous measurement (TG-DTA measurement) curve may vary in measured temperature depending on the temperature elevated per minute, the purity of a sample etc. In the present description, the term "around" means ±5.0° C.

Figure 1:
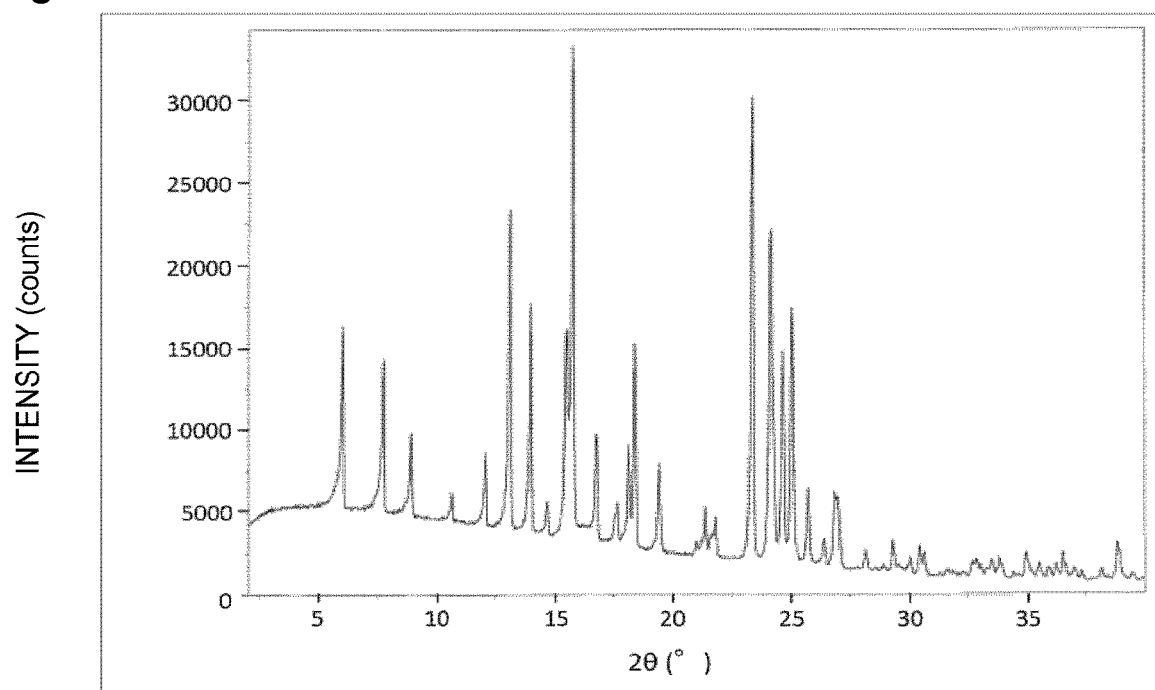
FIG. 1 shows an X-ray powder diffraction spectrum of Crystal I of Compound (I) obtained in Example 1 (the longitudinal axis shows intensity (counts) and the horizontal axis shows the diffraction angle (2θ)).
Figure 2:
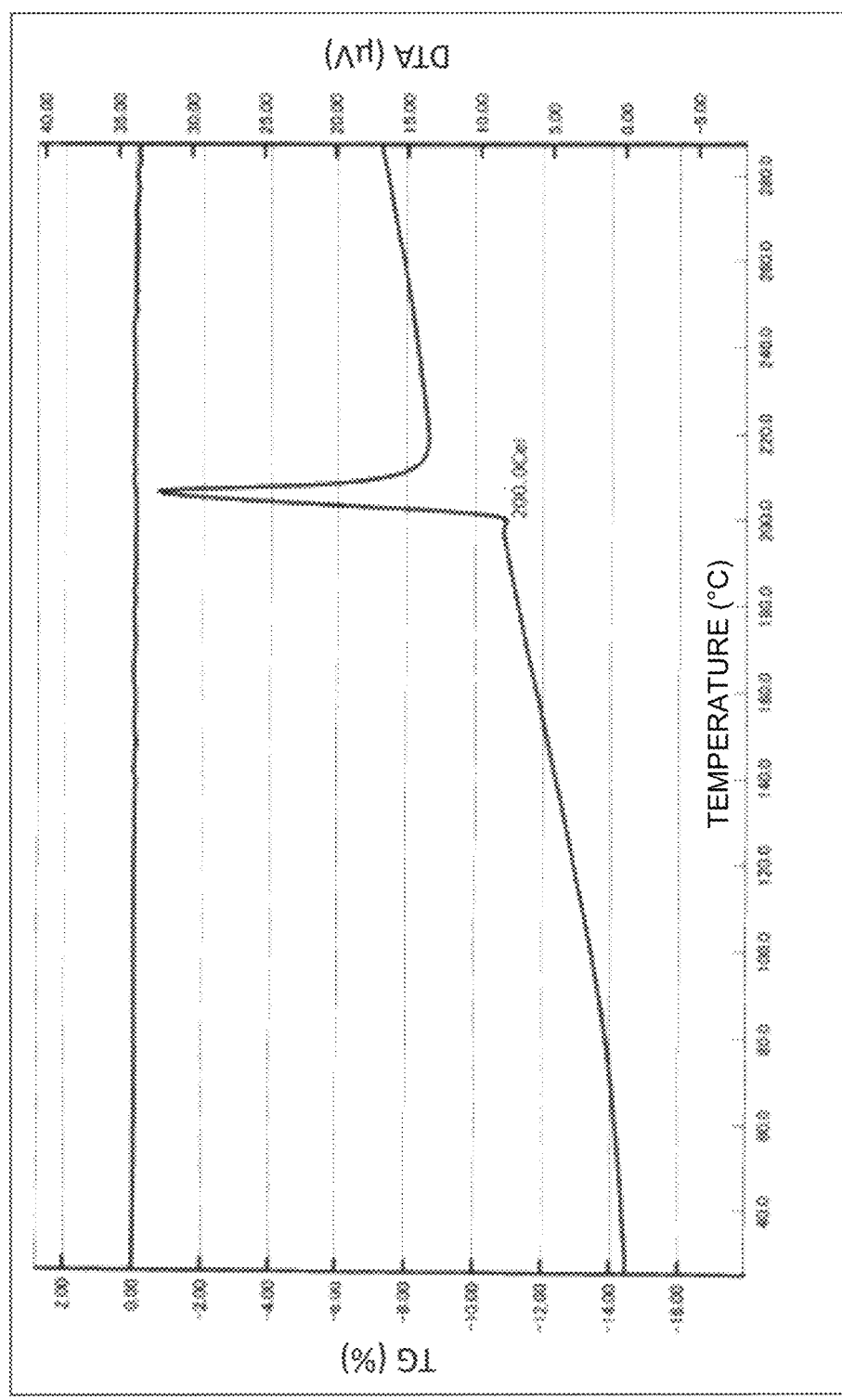
FIG. 2 shows a thermogravimetric-differential thermal simultaneous measurement (TG-DTA measurement) curve of Crystal I of Compound (I) obtained in Example 1.

Crystal I of Compound (I) has an X-ray powder diffraction spectrum as shown in FIG. 1, and a thermogravimetric-differential thermal simultaneous measurement (TG-DTA measurement) curve as shown in FIG. 2.

Here, the X-ray powder diffraction spectrum of Crystal I of Compound (I) has characteristic peaks at diffraction angles (2θ±0.2°) selected from the group consisting of 6.0°, 7.7°, 8.9°, 10.6°, 12.1°, 13.1°, 14.0°, 14.7°, 15.5°, 15.8°, 16.8°, 17.7°, 18.1°, 18.4°, 19.4°, 23.4°, 24.1°, 24.7°, 25.1° and 25.7°.

Crystal I of Compound (I) according to the present invention is a crystal having six or more peaks selected from the above-described peaks, preferably a crystal having eight or more peaks selected from the above-described peaks, more preferably a crystal having ten or more peaks selected from the above-described peaks, especially preferably a crystal having all of the above-described peaks.

The endothermic peak in the thermogravimetric-differential thermal simultaneous measurement (TG-DTA measurement) curve of Crystal I of Compound (I) is present around 198° C. to 202° C., preferably around 200° C.

Crystal I of Compound (I) according to the present invention can be manufactured by, for example, a method comprising step (1) of dissolving Compound (I) in a solvent, and step (2) of preparing solid Compound (I) by cooling the solution obtained in step (1).

As a crystallization solvent in step (1), 1-propanol etc. can be used.

It is preferable that the solution obtained in step (1) be cooled to room temperature or lower in step (2).

An appropriate amount of Crystal I of Compound (I) or a mixed crystal containing Crystal I may be added as a seed crystal for promoting crystallization of Crystal I. The amount of the seed crystal added is from 0.01 to 5 (w/v) %, preferably from 0.03 to 1 (w/v) %, of the amount of the solvent. Crystallization may be performed with stirring for reduction of the crystallization time and control of the particle size.

Crystal I of Compound (I) according to the present invention can also be manufactured by a method comprising step (3) of dissolving Compound (I) in a good solvent, and step (4) of preparing solid Compound (I) by adding a poor solvent in an amount three times the amount of the good solvent (v/v) to the solution obtained in step (3).

As the good solvent and the poor solvent, methanol (good solvent) and water (poor solvent), methanol (good solvent) and isopropyl ether (IPE) (poor solvent), methanol (good solvent) and heptane (poor solvent), ethanol (good solvent) and IPE (poor solvent), ethanol (good solvent) and heptane (poor solvent), 1-propanol (good solvent) and IPE (poor solvent), 1-propanol (good solvent) and heptane (poor solvent), 2-propanol (good solvent) and heptane (poor solvent), acetone (good solvent) and IPE (poor solvent), acetone (good solvent) and heptane (poor solvent), dimethyl sulfoxide (DMSO) (good solvent) and water (poor solvent), dimethylacetamide (DMA) (good solvent) and water (poor solvent), tetrahydrofuran (THF) (good solvent) and IPE (poor solvent), THF (good solvent) and heptane (poor solvent) etc. can be used. The amount of the poor solvent is preferably three times the amount of the good solvent (v/v).

The temperature at which Compound (I) is dissolved in the good solvent can be appropriately set. The temperature is preferably 65° C. when Compound (I) is dissolved in methanol or THF. The temperature is preferably 65° C. or 80° C. when Compound (I) is dissolved in ethanol or 1-propanol. The temperature is preferably 80° C. when Compound (I) is dissolved in 2-propanol. The temperature is preferably 50° C. when Compound (I) is dissolved in acetone. The temperature is preferably 40° C. when Compound (I) is dissolved in DMSO or DMA.

In step (4), Compound (I) can be precipitated at the above-described dissolution temperature, and if Compound (I) is not precipitated at the dissolution temperature, Crystal I can be obtained by cooling Compound (I) to 25° C.

The precipitated crystal can be isolated and purified from a dissolving solution, a mixed solution etc. of the crystal by, for example, known separation and purification means such as filtration, washing with water or drying under reduced pressure.

As shown in Examples below, Crystal I of Compound (I) according to the present invention is non-hygroscopic and has excellent solid stability (storage stability etc.). It is important that pharmaceutical candidates in development have solid stability in industrial operations and for keeping the quality.

Solvents to be used for manufacturing pharmaceuticals may have toxicity, and the amount of a solvents which remain after a manufacturing process is preferably as small as possible from the viewpoint of safety. In this regard, Crystal I of Compound (I) does not contain residual solvents in an amount equal to or larger than the regulatory value in ICH (International Council for Harmonization of Technical Requirements for Pharmaceuticals for Human Use) Guideline.

Therefore, Crystal I of Compound (I) according to the present invention has excellent natures required as a pharmaceutical or a drug substance for a pharmaceutical.

Crystal I of Compound (I) according to the present invention has excellent Her2 inhibitory activity, and is useful as a preventive agent and/or a therapeutic agent for diseases which involve Her2, for example cancers and tumors. In addition, Crystal I has the advantage of having very excellent selectivity on Her2, so that little side-effects occur due to inhibition of other kinases.

In the present description, "Her2" includes Her2 of humans or nonhuman mammals, and is preferably human Her2. The term "Her2" includes isoforms.

The "disease involving HER2" is a disease in which deletion, suppression and/or inhibition of the functions of HER2 reduces the incidence rate, and alleviates, mitigates and/or cures the symptom. Examples of the disease include, but are not limited to, malignant tumors. The disease is preferably a malignant tumor with excessive expression of HER2, amplification of HER2 gene or mutation of HER2. Examples of the "malignant tumor" concerned include, without limitation, head and neck cancer, esophageal cancer, gastric cancer, colon cancer, rectal cancer, hepatocarcinoma, gallbladder-bile duct cancer, biliary cancer, pancreatic cancer, lung cancer, breast cancer, ovarian cancer, cervical cancer, endometrial cancer, kidney cancer, bladder cancer, prostate cancer, testis tumor, bone and soft tissue sarcoma, blood cancer, multiple myeloma, skin cancer, brain tumor, and mesothelioma. The malignant tumor is preferably breast cancer, gastric cancer, esophageal cancer, ovarian cancer, lung cancer, gallbladder-bile duct cancer, biliary cancer, bladder cancer or colon cancer, more preferably breast cancer, gastric cancer, esophageal cancer, biliary cancer, ovarian cancer or lung cancer, still more preferably breast cancer or gastric cancer.

When Crystal I of Compound (I) is used as a medicament, Crystal I is ground or is nor ground, and a variety of administration forms can be employed depending on preventive or therapeutic purposes. The form may be, for example, any of oral agents such as a tablet, a capsule, a granule, a subtle granule, a powdered drug and a dry syrup; and parenteral agents such as a suppository base, an inhalant, a nasal preparation, an ointment, a patch and an injection, and is preferably an oral agent. Each of these pharmaceutical compositions can be manufactured by a common formulating method known to those skilled in the art, with the use of a pharmaceutically acceptable carrier.

As pharmaceutical carriers, a variety of organic or inorganic carrier substances common as preparation materials are used, and added as an excipient, a binder, a disintegrant, a lubricant and a coating agent in solid preparations; a solvent, a solubilizing agent, a suspending agent, a tonicity agent, a buffer and a soothing agent in liquid preparations etc. Preparation additives such as a preservative, an antioxidant, a colorant, a sweetener and a stabilizer can also be used as needed.

Examples of the excipient include lactose, white sugar, D-mannitol, starch, crystalline cellulose and calcium silicate.

Examples of the binder include hydroxypropylcellulose, methylcellulose, polyvinylpyrrolidone, maltose syrup powder and hypromellose.

Examples of the disintegrant include sodium carboxymethyl starch, carmellose calcium, croscarmellose sodium, crospovidone, low-substituted hydroxypropylcellulose and partially pregelatinized starch.

Examples of the lubricant include talc, magnesium stearate, sucrose fatty acid ester, stearic acid and sodium stearyl fumarate.

Examples of the coating agent include ethylcellulose, aminoalkyl methacrylate copolymers RS, hypromellose and white sugar.

Examples of the solvent include water, propylene glycol and physiological saline.

Examples of the solubilizing agent include polyethylene glycol, ethanol, α-cyclodextrin, macrogol 400 and polysorbate 80.

Examples of the suspending agent include carrageenan, crystalline cellulose carmellose sodium and polyoxyethylene hardened castor oil.

Examples of the tonicity agent include sodium chloride, glycerin and potassium chloride.

Examples of the pH adjuster/buffer include sodium citrate, hydrochloric acid, lactic acid, phosphoric acid and sodium dihydrogenphosphate.

Examples of the soothing agent include procaine hydrochloride and lidocaine.

Examples of the preservative include ethyl parahydroxybenzoate, cresol and benzalkonium chloride.

Examples of the antioxidant include sodium sulfite, ascorbic acid and natural vitamin E.

Examples of the colorant include titanium oxide, iron sesquioxide, food blue No. 1 and copper chlorophyll.

Examples of the corrigent include aspartame, saccharin, sucrose, 1-menthol and mint flavors.

Examples of the stabilizer include sodium pyrosulfite, sodium edetate, erythorbic acid, magnesium oxide and dibutyl hydroxytoluene.

When an oral solid preparation is prepared, an excipient, and a binder, a disintegrant, a lubricant, a colorant, a corrigent etc. as needed can be added to Crystal I of Compound (I), followed by manufacturing a tablet, a coated tablet, a granule, a powdered drug, a capsule etc. by a usual method.

The amount of Crystal I of Compound (I) to be added to each administration unit form varies depending on the symptom of a patient to be given Crystal I, the dosage form thereof etc., and is, in general, preferably from about 0.05 to 1,000 mg for an oral agent, from about 0.1 to 500 mg for an injection, or from about 1 to 1,000 mg for a suppository base or external preparation, per administration unit form.

The daily dosage amount of Crystal I of Compound (I) in a drug having a certain administration form varies depending on the symptom, body weight, age, sex etc. of a patient, and cannot be flatly determined. Normally, the daily amount per adult (body weight: 50 kg) may be about 0.05 to 5,000 mg, preferably 0.1 to 1,000 mg. It is preferable to administer this amount of Crystal (I) once or in about two or three doses a day.

EXAMPLES

While the present invention will be described more specifically below with reference to Examples, the present invention is not limited by them in any way. While the present invention has been described enough by Examples, it is to be understood that different changes and/or modifications can be made by those skilled in the art. Therefore, such changes and/or modifications are encompassed by the present inventions, as long as they do not depart from the scope of the present invention.

A variety of reagents used in Examples were commercially available, unless otherwise specified. A NMR spectrum was measured by using tetramethylsilane as an internal standard when tetramethylsilane is included in a deuterated solvent and using a peak for non-deuterated protons remaining the NMR solvent as an internal standard otherwise, with the use of AL400 (400 MHz; JEOL Ltd.). All δ values are indicated in ppm.

The meanings of abbreviation are shown below.
s: Singlet
d: Doublet
t: Triplet
dd: Double Doublet
m: Multiplet
brs: Broad Singlet
DMSO-$d_6$: Deuterated Dimethyl Sulfoxide
$CDCl_3$: Deuterated Chloroform X-Ray Powder Diffraction Measurement X-ray powder diffraction was measured in accordance with any of the following test conditions after lightly grinding a suitable amount of test material by an agate mortar as needed.
Instrument: PANalytical Empyrean
  Target: Cu
  X-ray output setting: 40 mA, 45 kV
  Scanning range: 2.0-40.0°
  Step size: 0.026°
Instrument: Rigaku MiniFlex II
  Target: Cu
  X-ray output setting: 15 mA, 30 kV
  Scanning range: 2.0-40.0°
  Step size: 0.010°
  Scan speed: 5.00°/min
  Diverging slit: 1.25°
  Scattering slit: Open Handling of instruments including data processing was performed in accordance with the method and procedure indicated by each instrument.

The values obtained from a variety of spectra may slightly vary depending on the crystal growth direction, the particle size and measurement conditions. Those values thus should not be construed strictly.

Thermogravimetric-Differential Thermal Simultaneous Measurement (TG-DTA Measurement)

TG-DTA measurement was performed in accordance with the following test conditions.
Instrument: Hitachi High-Tech Science TG/DTA7200
  Sample: around 5 mg
  Sample container: made of aluminum
  Heating rate: heating at 10° C./min to 300° C.
  Atmosphere gas: Air
  Nitrogen gas flow rate: 100 mL/min Handling of instruments including data processing was performed in accordance with the method and procedure indicated by each instrument.

Example 1: Manufacturing of Crystal I of Compound (I) by Cooling Method

Compound (I) (200 mg) obtained by the method described in International Publication No. WO2017/038838 was suspended in 1-propanol (4 mL), and the suspension was heated to an external temperature of 100° C. to dissolve the compound. The solution was allowed to cool to room temperature, and then stirred overnight. The thus-obtained solid was collected by filtration, and dried at 70° C. under reduced pressure to obtain Crystal I (133 mg).

The obtained compound gave the following $^1$H-NMR spectrum. 1H NMR (400 MHz, DMSO-d6) δ: 1.52-1.69 (m, 1H), 1.92-2.03 (m, 1H), 2.06-2.41 (m, 2H), 2.10 (s, 3H), 2.13 (s, 3H), 2.85 (s, 3H), 2.99-3.24 (m, 1H), 3.05 (s, 3H), 3.29-3.85 (m, 1H), 3.33 (s, 2H), 3.99-4.58 (m, 2H), 4.67-4.81 (m, 1H), 5.58-5.73 (m, 1H), 6.05-6.15 (m, 1H), 6.71-6.96 (m, 1H), 6.95 (d, J=8.0 Hz, 1H), 7.10-7.15 (m, 1H), 8.09 (br s, 1H), 8.26 (s, 1H), 8.60 (br s, 1H), 10.11-10.24 (m, 1H).

Example 2: Manufacturing of Crystal I of Compound (I) by Poor Solvent Method

The good solvents and the poor solvents shown in Table 1 below were used. Compound (I) was dissolved in the good solvent. After observing dissolution of the compound at a set temperature, the poor solvent was added in an amount three times the amount of the good solvent (v/v). The dissolution temperature was kept when precipitation was observed, and the solution was cooled to 25° C. when precipitation was not observed. In this way, Crystal I was obtained.

TABLE 1

| Good solvent | Poor solvent | Dissolution temperature (° C.) | Precipitation temperature (° C.) |
| --- | --- | --- | --- |
| Methanol | Water | 65 | 65 |
| Methanol | IPE | 65 | 65 |
| Methanol | Heptane | 65 | 65 |
| Ethanol | IPE | 65 | 25 |
| Ethanol | Heptane | 80 | 25 |
| 1-Propanol | IPE | 65 | 25 |
| 1-Propanol | Heptane | 80 | 80 |
| 2-Propanol | Heptane | 80 | 25 |
| Acetone | IPE | 50 | 50 |
| Acetone | Heptane | 50 | 50 |
| DMSO | Water | 40 | 40 |
| DMA | Water | 40 | 40 |
| THF | IPE | 65 | 65 |
| THF | Heptane | 65 | 65 |

The X-ray powder diffraction spectrum of Crystal I precipitated is shown in FIG. 1, and characteristic diffraction angles are as follows.
Characteristic diffraction angles (2θ±0.2°): 6.0°, 7.7°, 8.9°, 10.6°, 12.1°, 13.1°, 14.0°, 14.7°, 15.5°, 15.8°, 16.8°, 17.7°, 18.1°, 18.4°, 19.4°, 23.4°, 24.1°, 24.7°, 25.1° and 25.7°
The results of thermogravimetric-differential thermal simultaneous measurement (TG-DTA measurement) of Crystal I were as follows.
Thermogravimetric-differential thermal simultaneous measurement (TG-DTA measurement) curve: shown in FIG. 2
Endothermic peak in thermogravimetric-differential thermal simultaneous measurement (TG-DTA measurement) curve: around 200° C.

Example 3: Single-Crystal Analysis of Crystal I

100 μL of methanol was added to Compound (I) to dissolve the compound, and IPE was then gradually mixed at room temperature by vapor diffusion. Diffraction of Crystal I was observed after a week.
Color of crystal: Colorless
Crystal shape: Plate shape
The obtained Crystal I was shaped to 0.30×0.26×0.20 mm, measurement was performed under the following conditions, and data processing was performed as described below.
Instrument: VariMax DW with RAPID (Rigaku Corporation)
Data measurement/processing software: RAPID AUTO
Structure analysis program packaging: CrystalStructure
Integrated X-ray powder analysis software: PDXL
X-ray source: Cu Kα (λ=1.54187 Å)
Tube voltage-tube current: 40 kV-30 mA
Measurement temperature: −180° C. (using a spraying low-temperature apparatus)
Collimator diameter: Φ0.5 mm
Camera length: 127.4 mm
Oscillation angle: 15°
Exposure time: 60 sec/piece
Total number of measured pieces: 156 (12×13 series)
Total measurement time: 6 hours and 57 minutes (including reading time)
Crystal data are shown below.
Crystal system: monoclinic system
Lattice type: P
Laue group: 2/m
Space group: P2$_1$ Lattice constant:
a=11.5696(2) Å
b=7.47792(14) Å
c=14.6722 (3) Å
β=100.674(7°)
Volume of unit lattice: V=1247.43(5) Å$^3$.
2θmax: 136.4°
Number of observed reflections: 38021
Integrity: 100.0%
R merge: 2.25%
I/sig (I) (lastshell): 24.2 (34.1)
The result of performing simulation of the X-ray diffraction pattern on the basis of the obtained result of structure analysis revealed that the same X-ray diffraction pattern as that of Crystal I was obtained.

Comparative Example 1: Manufacturing of Crystal II of Compound (I)

Figure 3:
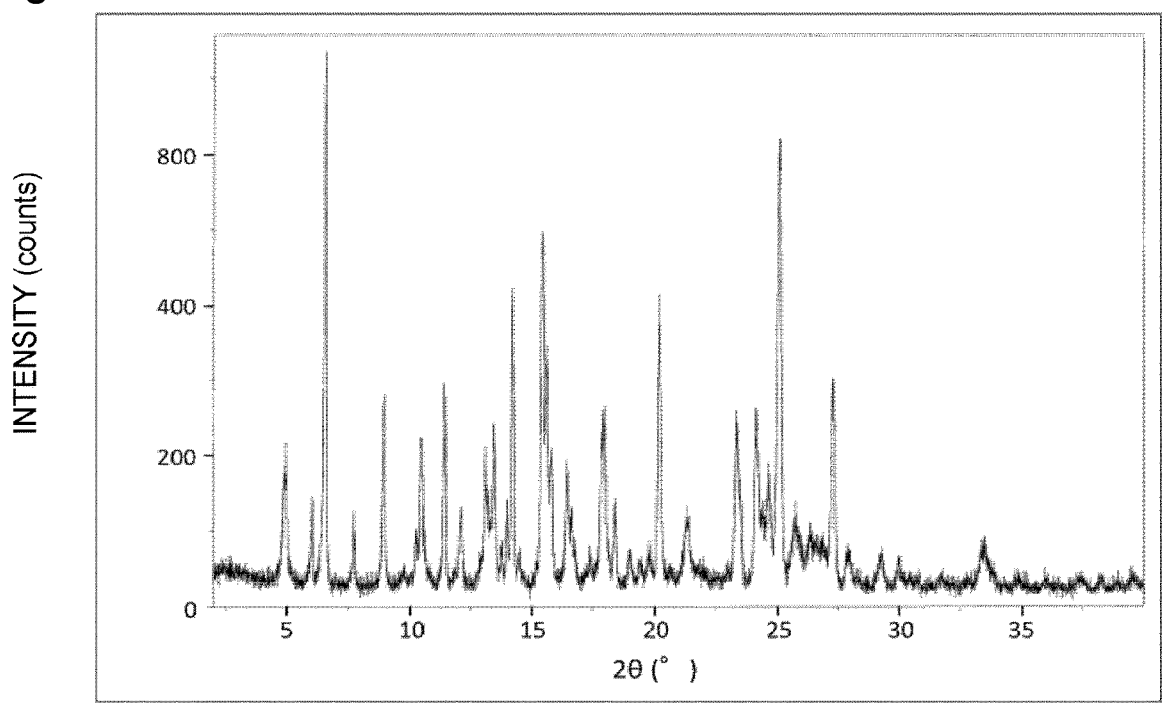
FIG. 3 shows an X-ray powder diffraction spectrum of Crystal II of Compound (I) obtained in Comparative Example 1 (the longitudinal axis shows intensity (counts) and the horizontal axis shows the diffraction angle (2θ)).
Figure 4:
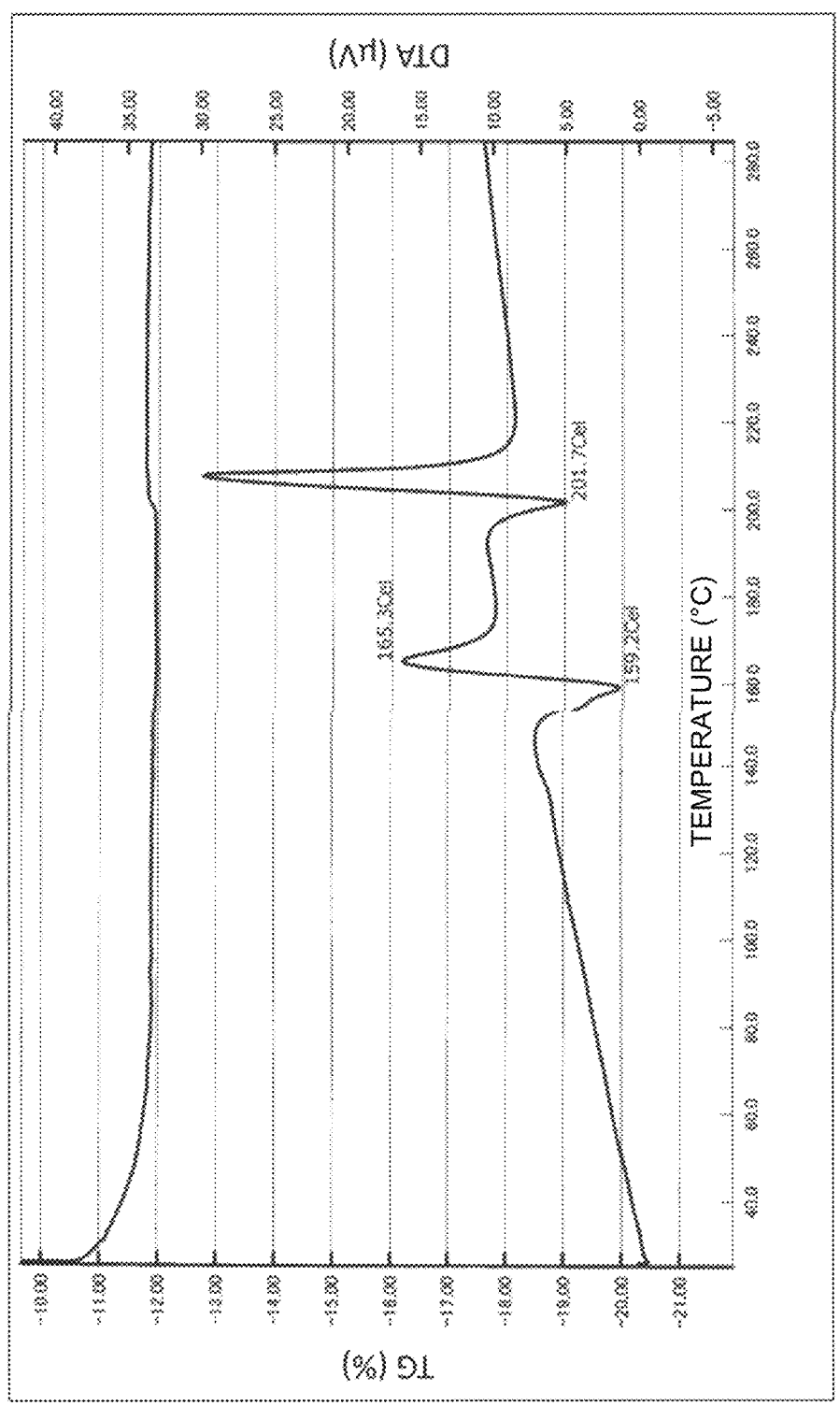
FIG. 4 shows a thermogravimetric-differential thermal simultaneous measurement (TG-DTA measurement) curve of Crystal II of Compound (I) obtained in Comparative Example 1.

Compound (I) (100 mg) obtained by the method described in International Publication No. WO2017/038838 was dissolved in a mixed solution of ethanol (9 mL) and water (1 mL). Thereafter, the solvent was removed by distillation under reduced pressure at 40° C. The obtained solid was dried under reduced pressure to obtain Crystal II.
The X-ray powder diffraction spectrum and the thermogravimetric-differential thermal simultaneous measurement (TG-DTA measurement) curve of the obtained Crystal II are as follows.
X-ray powder diffraction spectrum: shown in FIG. 3
Characteristic diffraction angles (2θ±0.2°): 5.0°, 6.6°, 9.0°, 11.4°, 14.2°, 15.4°, 20.2°, 23.4°, 25.1° and 27.3°
Thermogravimetric-differential thermal simultaneous measurement (TG-DTA measurement) curve: shown in FIG. 4

Comparative Example 2: Manufacturing of Crystal III of Compound (I)

Figure 5:
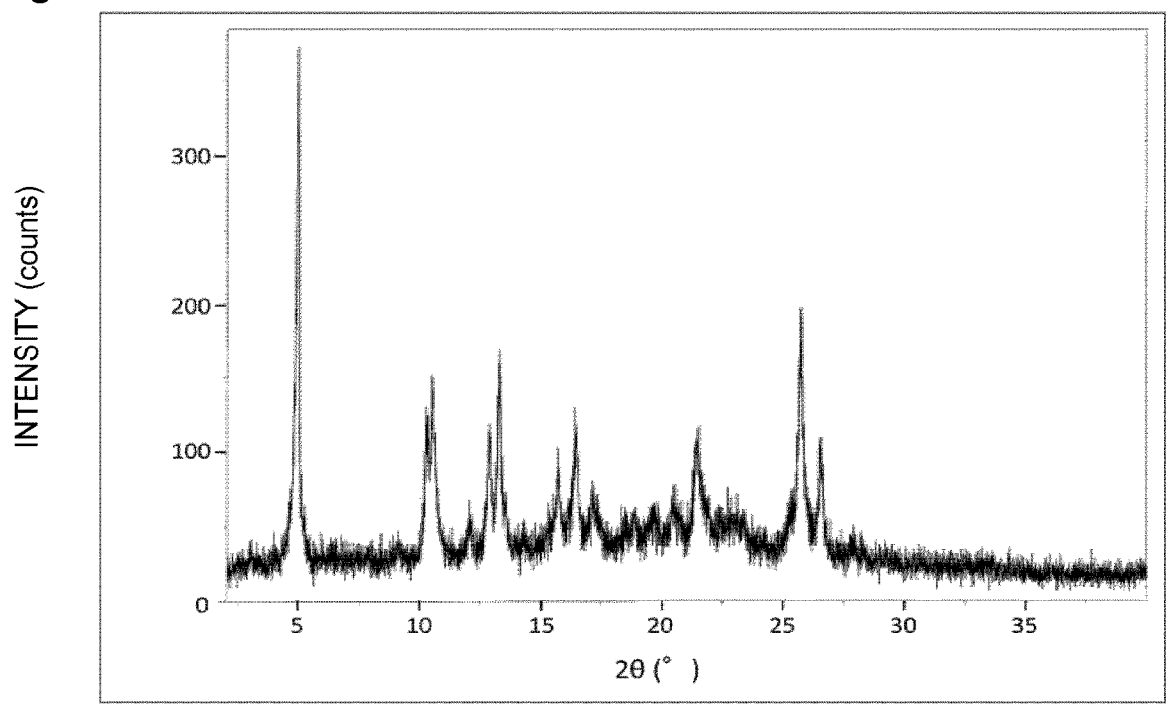
FIG. 5 shows an X-ray powder diffraction spectrum of Crystal III of Compound (I) obtained in Comparative Example 2 (the longitudinal axis shows intensity (counts) and the horizontal axis shows the diffraction angle (2θ)).
Figure 6:
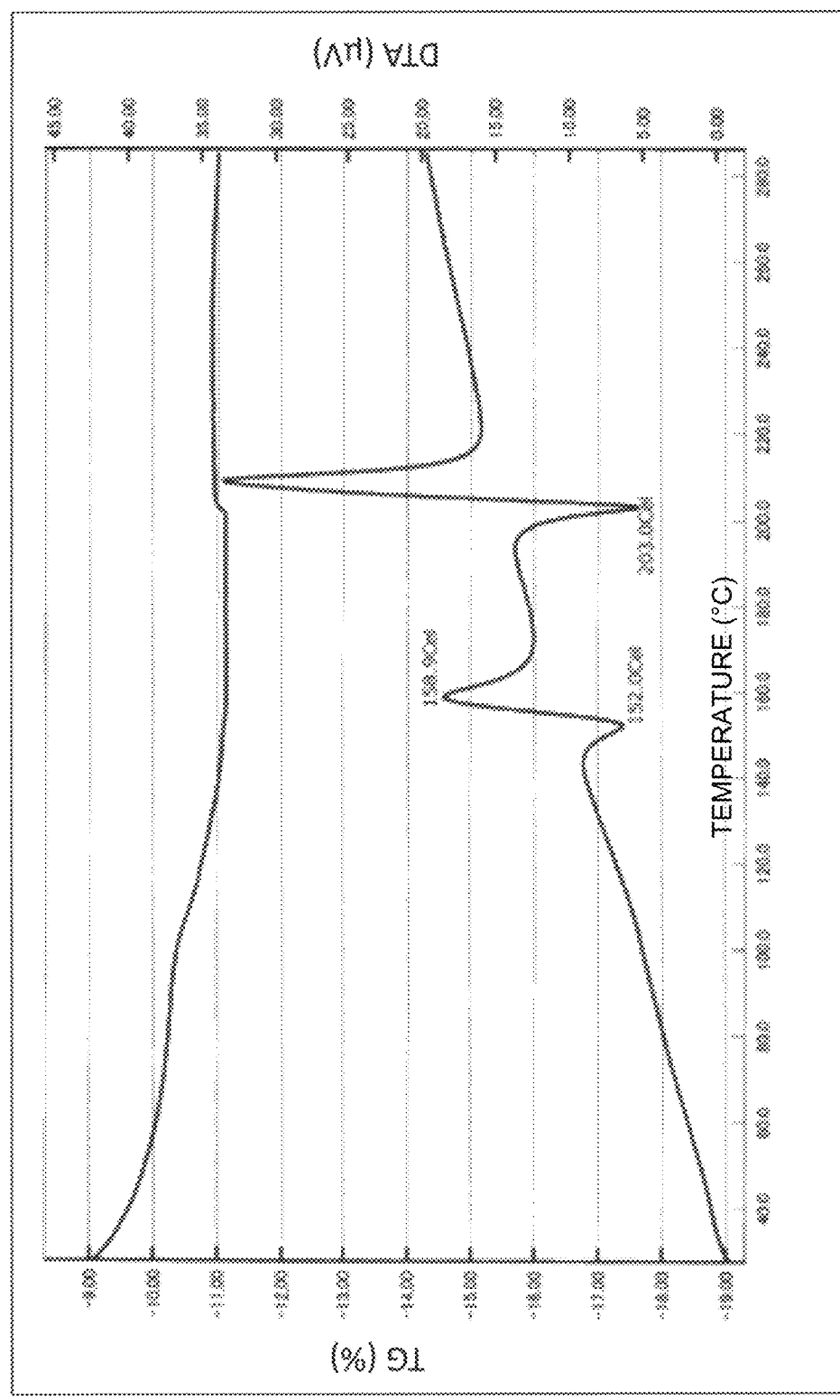
FIG. 6 shows a thermogravimetric-differential thermal simultaneous measurement (TG-DTA measurement) curve of Crystal III of Compound (I) obtained in Comparative Example 2.

Compound (I) (100 mg) obtained by the method described in International Publication No. WO2017/038838 was dissolved in methanol (10 mL). Thereafter, the solvent was removed by distillation under reduced pressure at 40° C. The obtained solid was dried under reduced pressure to obtain Crystal III.
The X-ray powder diffraction spectrum and the thermogravimetric-differential thermal simultaneous measurement (TG-DTA measurement) curve of the obtained Crystal III are as follows.
X-ray powder diffraction spectrum: shown in FIG. 5
Characteristic diffraction angles (2θ±0.2°): 5.0°, 10.3°, 10.5°, 12.9°, 13.3°, 15.7°, 16.4°, 21.5°, 25.7° and 26.5°
Thermogravimetric-differential thermal simultaneous measurement (TG-DTA measurement) curve: shown in FIG. 6

Test Example 1: Thermal Stability Test

A thermal stability test was conducted on Crystal I and Crystal III obtained in Example and Comparative Example described above. Crystal II was not reproduced, and it was not possible to conduct a thermal stability test.
X-ray powder diffraction measurement was performed at 25° C., and the temperature was elevated to 50° C. over 30 minutes, followed by performing X-ray powder diffraction measurement. The temperature was further elevated to 200° C. at 10° C./10 min, followed by performing X-ray powder diffraction measurement, then the temperature was lowered to 25° C. over 30 minutes, followed by performing X-ray powder diffraction measurement.

The results revealed that there was no change in crystal form of Crystal I under heating to 200° C., and the crystal was stable. On the other hand, the crystal form of Crystal III was changed by heating, and did not turn to the crystal form of Crystal III even when the crystal was cooled to 25° C.

Test Example 2: Solid Stability Test

The storage stability of Crystal I obtained in Example above was examined under the following conditions.
Storage conditions: 40° C./75° RH (open system and closed system), 60° C. (closed system), light shielding
Measurement point: 1 month
Storage amount: about 50 mg
Storage container: Brown glass bottle
X-ray powder diffraction measurement of the sample after storage was performed by the above-described method. For a change in mass of related substances (amount of detected substances other than Compound (I)), about 1 mg of the sample was weighed, and dissolved in about 5 mL of a water/acetonitrile mixed liquid (1:1), and 5 μL of the liquid was accurately measured and taken, and analyzed by HPLC in accordance with the following method.
Column: InertSustain C18 HP, 4.6×150 mm, 3 μm
Column temperature: 40° C.
Column flow rate: 0.8 mL/min
Mobile phase: A: 10 mM phosphate buffer (pH 6.8)/ acetonitrile (17:3) and B: acetonitrile/methanol (17:3)
Detection UV: 220 nm
Gradient:

| Time (min) | A | B |
|---|---|---|
| 0-30 | 95%→40% | 5%→60% |
| 30-40 | 40% | 60% |
| 40-41 | 40%→95% | 60%→5% |
| 41-45 | 95% | 5% |

The results revealed that for Crystal I, there was no change in X-ray powder diffraction pattern, and the crystal was very stable. As shown in Table 2 below, Crystal I had little related substances, and did not change in appearance.

TABLE 2

|  | Stability | |
|---|---|---|
| Conditions | Related substances | Appearance |
| 40° C./75% RH (open system) | <0.1% | No change |
| 40° C./75% RH (closed system) | <0.1% | No change |
| 60° C. (closed system) | <0.1% | No change |
| Light shielding (1,200,000 lx · hr) | <0.1% | No change |

Test Example 3: Dynamic Moisture Absorption/Desorption Test

In the test, VTI-SA+(TA Instruments) was used. About 10 mg of crystal I was weighed, and put into a pan. The temperature was elevated at a rate of 1 degree per minute to 60° C. while observing the weight variation per 5 minutes of 0.0100% or less. When the weight varied, this temperature was maintained for a maximum of 5 hours, followed by starting the next step. Thereafter, the temperature was cooled to 25° C., and the humidity was increased from 5% RH to 95% RH, and then decreased to 5% RH. Here, the humidity was increased in increments of 5% RH while observing the weight variation per 5 minutes of 0.00100% or less. When the weight varied, this humidity was maintained for a maximum of 2 hours, followed by starting the next step.

Figure 7:
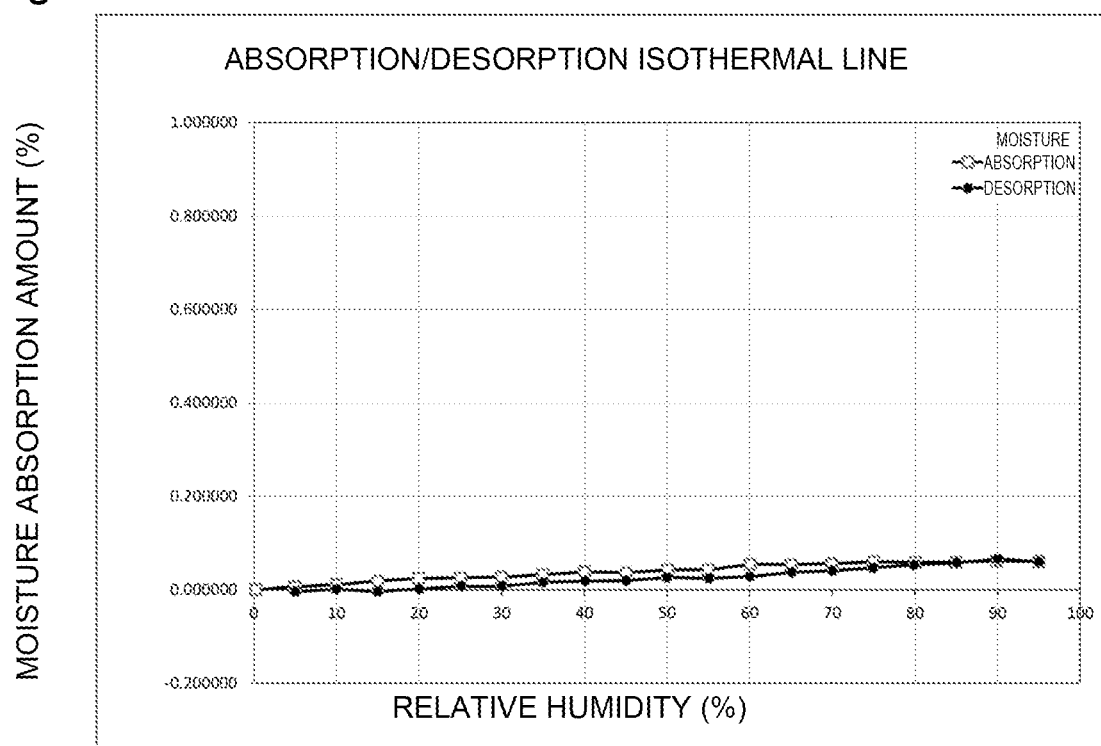
FIG. 7 shows a moisture absorption/desorption isothermal line of Crystal I of Compound (I) obtained in Example 1.
Figure 8:
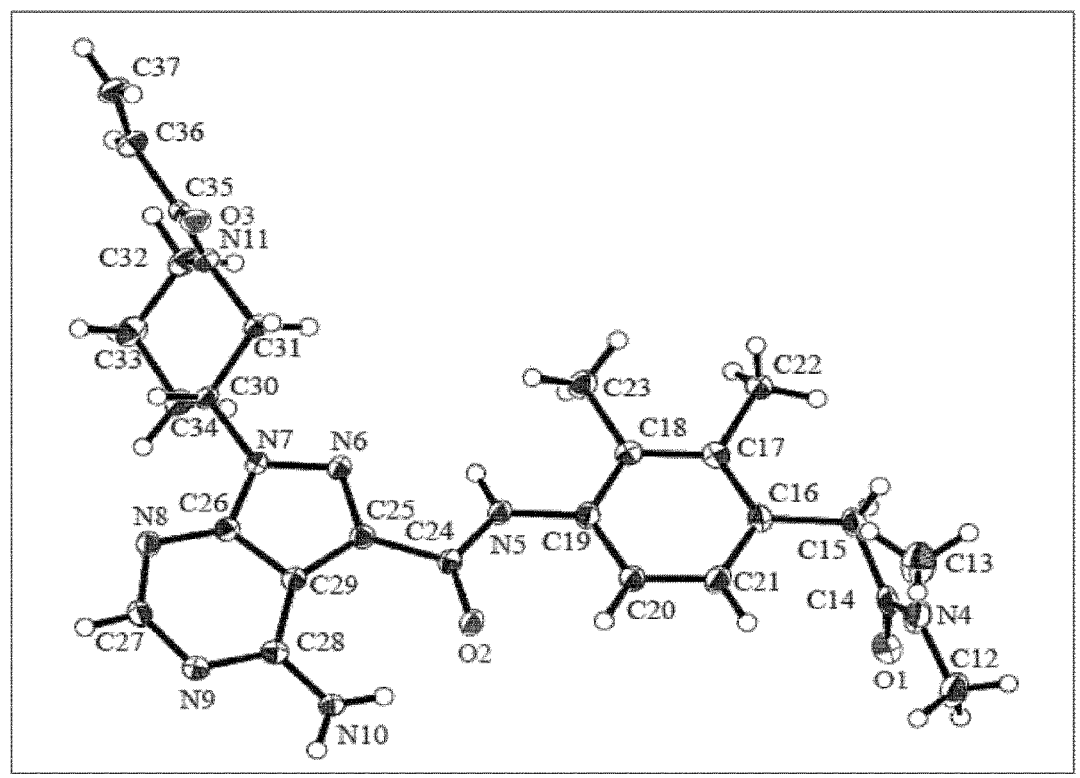
FIG. 8 shows a molecular structure diagram of Compound (I) obtained in Example 3.
Figure 9:
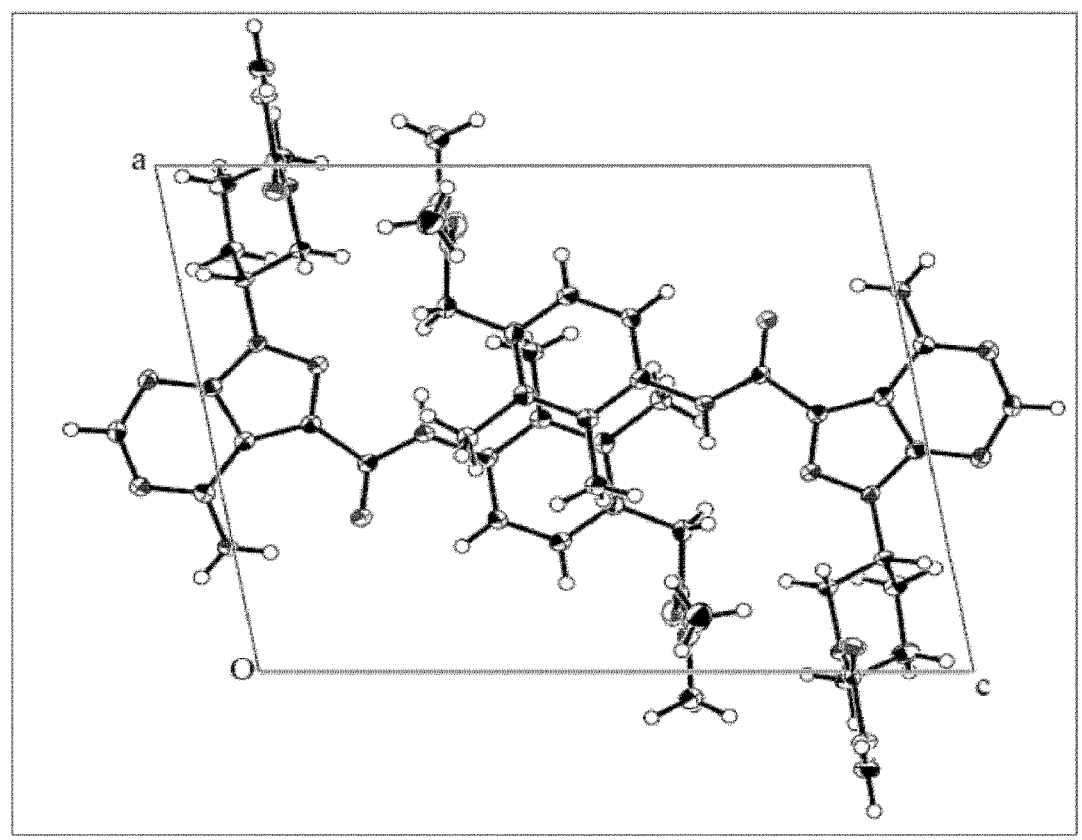
FIG. 9 shows a packing diagram (b-axis projection) of Compound (I) obtained in Example 3.

As shown in FIG. 7, Crystal I was observed to be non-hygroscopic.

The invention claimed is:

1. A crystal of (R)-1-(1-acryloylpiperidin-3-yl)-4-amino-N-(4-(2-(dimethylamino)-2-oxoethyl)-2,3-dimethylphenyl)-1H-pyrazolo[3,4-d]pyrimidine-3-carboxamide having an X-ray powder diffraction spectrum having at least six peaks at diffraction angles (2θ±0.2°) selected from the group consisting of 6.0°, 7.7°, 8.9°, 10.6°, 12.1°, 13.1°, 14.0°, 14.7°, 15.5°, 15.8°, 16.8°, 17.7°, 18.1°, 18.4°, 19.4°, 23.4°, 24.1°, 24.7°, 25.1° and 25.7°.

2. The crystal according to claim 1, wherein the crystal has an X-ray powder diffraction spectrum having peaks at diffraction angles (2θ±0.2°) of 6.0°, 7.7°, 8.9°, 10.6°, 12.1°, 13.1°, 14.0°, 14.7°, 15.5°, 15.8°, 16.8°, 17.7°, 18.1°, 18.4°, 19.4°, 23.4°, 24.1°, 24.7°, 25.1° and 25.7°.

3. The crystal according to claim 1, wherein an endothermic peak is present at a peak temperature of around 200° ° C. in thermogravimetric-differential thermal simultaneous measurement (TG-DTA measurement).

4. The crystal according of claim 1, wherein the crystal has the following crystal data in single-crystal analysis:
crystal system: single-crystal system
space group: $P2_1$
lattice constant:
a=11.5696(2) Å
b=7.47792(14) Å
c=14.6722(3) Å
β=100.674(7)°
Volume of unit lattice: V=1247.43(5) Å$^3$.

5. A pharmaceutical composition comprising the crystal of claim 1.

6. A pharmaceutical composition for oral administration, comprising the crystal of claim 1.

7. A method for treating a malignant tumor with excessive expression of HER2, amplification of HER2 gene or mutation of HER2, comprising administering an effective amount of the crystal of claim 1 to a patient in need thereof.

8. A method of manufacturing a pharmaceutical composition comprising combining the crystal of claim 1 with one or more pharmaceutically acceptable excipients.

* * * * *